US009756972B2

United States Patent
Gogue-Meunier et al.

(10) Patent No.: US 9,756,972 B2
(45) Date of Patent: Sep. 12, 2017

(54) ASSISTANCE SYSTEM FOR FITTING A MEDICAL COMPRESSION DEVICE ONTO A LIMB OF A PATIENT

(71) Applicant: BELOVIA, Autun (FR)

(72) Inventors: Guillaume Gogue-Meunier, Reclesne (FR); Romain Truong, Autun (FR); Joël M. Chevalier, Sussey (FR)

(73) Assignee: BELOVIA, Autun (FR)

( * ) Notice: Subject to any disclaimer, the term of this patent is extended or adjusted under 35 U.S.C. 154(b) by 0 days.

(21) Appl. No.: 15/311,771

(22) PCT Filed: May 13, 2015

(86) PCT No.: PCT/FR2015/051249
§ 371 (c)(1),
(2) Date: Nov. 16, 2016

(87) PCT Pub. No.: WO2015/173512
PCT Pub. Date: Nov. 19, 2015

(65) Prior Publication Data
US 2017/0079455 A1    Mar. 23, 2017

(30) Foreign Application Priority Data
May 16, 2014  (FR) ...................................... 14 54414

(51) Int. Cl.
*A47G 25/90* (2006.01)
*A61F 13/08* (2006.01)

(52) U.S. Cl.
CPC ............ *A47G 25/905* (2013.01); *A61F 13/08* (2013.01)

(58) Field of Classification Search
CPC .... A47G 25/90; A47G 25/905; A47G 25/907; A47G 25/908
(Continued)

(56) References Cited

U.S. PATENT DOCUMENTS

| 4,066,194 A * | 1/1978 | Leland | A47G 25/905 223/111 |
| 4,284,216 A * | 8/1981 | Leland | A47G 25/905 223/111 |

(Continued)

FOREIGN PATENT DOCUMENTS

| FR | 2 921 552 A1 | 4/2009 |
| WO | 2012/032459 A1 | 3/2012 |

OTHER PUBLICATIONS

Aug. 10, 2015 Search Report issued in International Patent Application No. PCT/FR2015/051249.
(Continued)

Primary Examiner — Nathan Durham
(74) Attorney, Agent, or Firm — Oliff PLC

(57) ABSTRACT

An assistance system including a support and two stretching members wherein a retaining part and a base of at least a first of the stretching members extend respectively in transverse planes, the transverse plane containing the retaining part of the first stretching member being offset towards the retaining part of the second stretching member relative to the base of said first stretching member, and wherein the first stretching member includes: a shaped rod and having a bow for forming a body having a recess, an external connecting element to which the base is linked, and an internal connecting element parallel to the external connecting element.

13 Claims, 4 Drawing Sheets

(58) Field of Classification Search
USPC .................................................. 223/111–112
See application file for complete search history.

(56) References Cited

U.S. PATENT DOCUMENTS

| | | | | |
|---|---|---|---|---|
| 4,942,988 | A * | 7/1990 | Doorenbos | A47G 25/905 223/111 |
| 5,632,424 | A * | 5/1997 | Maier | A47G 25/905 223/111 |
| 7,395,951 | B2 * | 7/2008 | Clayman | A47G 25/905 223/111 |
| 2007/0084890 | A1 | 4/2007 | Clayman | |
| 2010/0264678 | A1 * | 10/2010 | Rolling, Jr. | A47G 25/005 294/2 |

OTHER PUBLICATIONS

Aug. 10, 2015 Written Opinion issued in International Patent Application No. PCT/FR2015/051249.

* cited by examiner

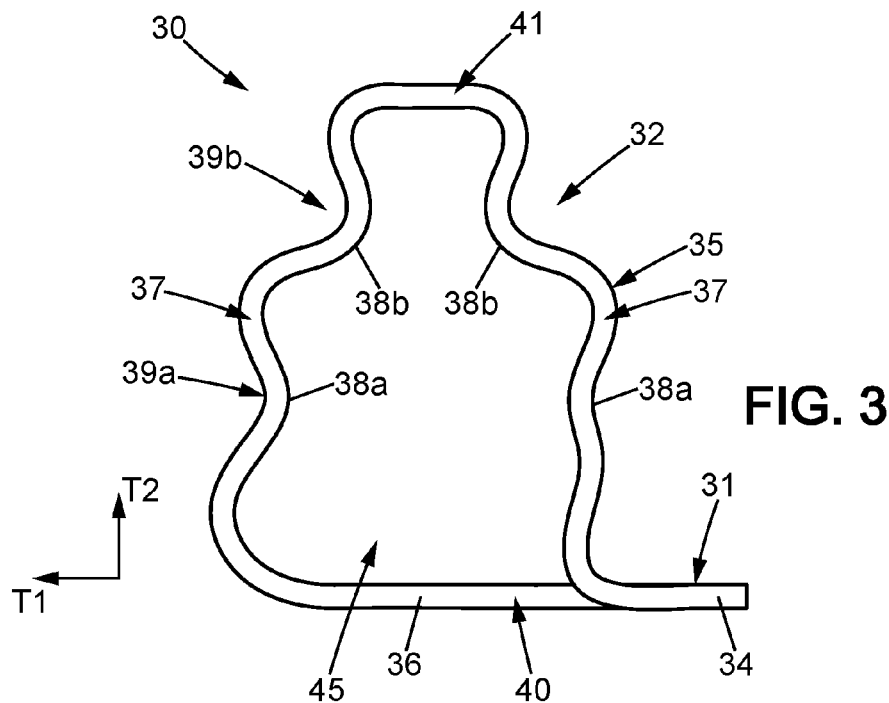
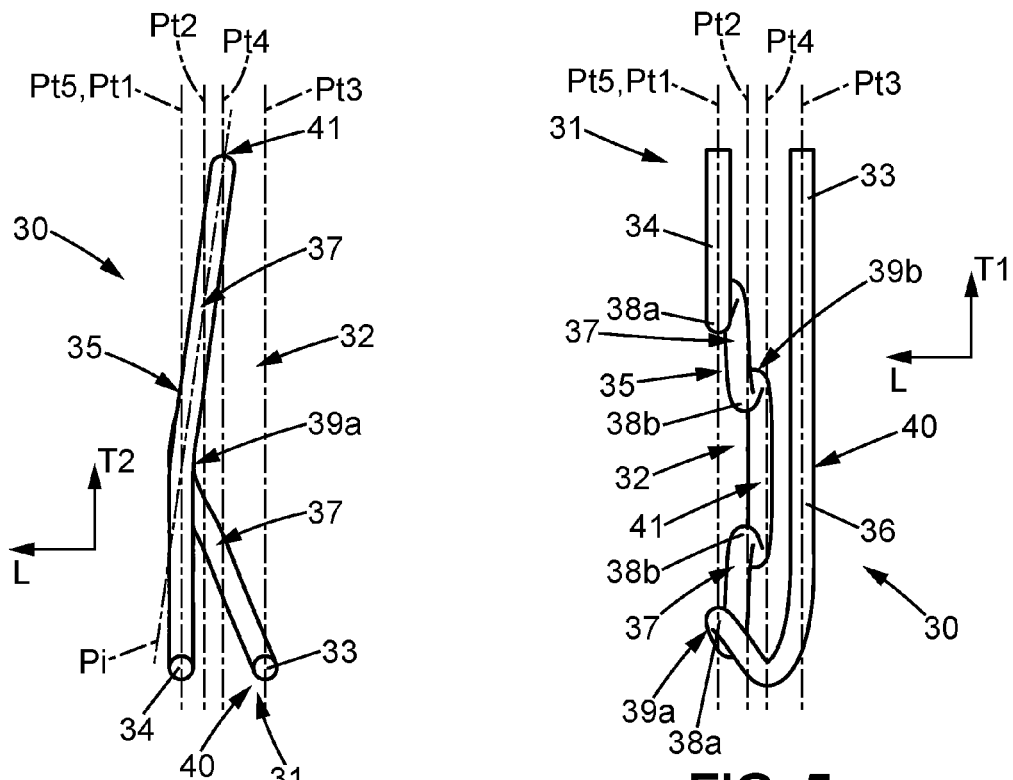

ASSISTANCE SYSTEM FOR FITTING A MEDICAL COMPRESSION DEVICE ONTO A LIMB OF A PATIENT

FIELD OF THE DISCLOSURE

The invention relates to an assistance system for fitting a medical compression device onto a limb of a patient.

The invention relates in particular to the fitting of a medical compression device that has the form of medical compressions stockings or support stockings onto a lower limb of the patient.

BACKGROUND OF THE DISCLOSURE

Support stockings are used in patients, generally older, in particular in the framework of treating vascular pathologies and, in particular, in the framework of the treatment of the chronic venous disease of the lower limbs.

The fitting of support stockings requires providing a substantial effort in order to sufficiently separate the support stockings in such a way as to allow the foot to pass, then to slide the support stockings along the leg. This effort can be all the more so substantial when the limb on which the support stockings must be placed is wet, in particular after the bathing of the patient, or covered with a product, a textile layer or other, in particular after care carried out on the patient. In addition to the extent of it, the effort may have to be exerted according to different orientations that are sometimes not very natural, in particular when the patient has lost flexibility and cannot extend the foot and/or raise the leg.

The patients themselves generally no longer having dexterity, force and the flexibility required for the fitting of the support stockings, this gesture can be entrusted to an assistant such as a caregiver, home help, a nurse or other.

However, the assistant may need to repeat this physically demanding gesture a great number of times. Such a repetition can lead to muscular and/or joint disorders in the assistant and can dissuade the assistant from practicing all of the treatment and care required for the patient.

In order to simplify the fitting of the support stockings by the patient as well as by the assistant, assistance systems, known under the name of stocking puller, have been designed.

Such assistance systems are, for example, described in documents FR 2 818 883 and FR 2 951 059. They comprise two stretching members mounted on a support facing one another and which can be displaced with respect to one another in translation. Each stretching member comprises one or several retaining parts on each one of which at least one portion of the support stockings, in the vicinity of a fitting opening of the latter, can be positioned when the stretching members are brought closer to one another, and stretched when the stretching members are separated from one another.

However, the known assistance systems always require the user, patient or assistant, to exert a substantial effort in order to sufficiently separate the stretching members and to maintain them in position in such a way as to allow for the fitting of the support stockings.

In the same way, document US 2007/0084890 describes an assistance system comprising stretching members of which the conformation requires substantially separating them from one another in order to allow for the passage of the limb and, in particular, of the foot.

SUMMARY OF THE DISCLOSURE

The invention aims to improve the known assistance systems.

To this effect, the invention proposes an assistance system for fitting a medical compression device onto a limb of a patient, the medical compression device having a fitting opening, with the assistance system comprising:

a support extending along a longitudinal axis, two stretching members each comprising a connecting arm extending from the support along a first transversal direction, and a body extending from the connecting arm along a second transversal direction, with the body of each one of the stretching members comprising a base linked to the connecting arm and at least one retaining part separated from the base and whereon at least one part of the medical compression device in the vicinity of the fitting opening is intended to be positioned, with the stretching members being mounted on the support facing another and moveable with respect to one another in translation along the longitudinal axis, wherein the retaining part and the base of at least a first of the stretching members extend respectively in transverse planes perpendicular to the longitudinal axis, the transverse plane containing the retaining part of the first stretching member being offset along the longitudinal axis towards the retaining part of the other, second, stretching member relative to the transversal plane containing the base of said first stretching member, the body of the first stretching member having a recess along the second transversal direction at least on the retaining part, and wherein the first stretching member comprises:

a shaped rod for forming the body and comprising the base of the body, an external connecting element extending along the first transversal direction for forming a part of the connecting arm, with the base of the body being linked to the external connecting element, and an internal connecting element extending along the first transversal direction parallel to the external connecting element, the internal connecting element being offset from the external connecting element along the longitudinal axis in the direction of the second stretching member, the internal connecting element forming another part of the connecting arm to which the rod is linked opposite the base.

As such, the stretching members can be placed in a plurality of relative positions in each one of which the bases of the stretching members are separated from one another by a separation that exceeds a separation between the retaining parts. Such an enlarging of the passage between the bases of the stretching members combined with the recess of at least one of the stretching members makes it possible to ensure the introduction of the limb, and in particular of the foot, of the patient between the stretching members while still reducing the separation required between the stretching members in order to fit the medical compression device. The efforts required to separate and maintain the medical compression device can as such be reduced.

The body of the first stretching member can have a concavity oriented in a direction opposite the second stretching member on the retaining part of said first stretching member.

In particular, the retaining part of the first stretching member can have a fold extending along the first transversal direction.

The body of each one of the stretching members can have a distal end opposite the base, the retaining part of the first stretching member being offset along the longitudinal axis towards the retaining part of the second stretching member in relation to the distal end of said first stretching member.

The distal end of the first stretching member can be arranged between two transversal planes wherein extend respectively the base and the retaining part of said first stretching member.

In an embodiment, the first stretching member can be formed of a single piece by the shaped rod (in particular folded or arched), the rod comprising an external branch forming the external connecting element, and a bow extending globally along the second transversal direction for forming the body, the bow comprising a base branch extending in the extension of the external branch for forming the base of the body.

The rod can then further comprise an internal branch forming the internal connecting element.

The rod can be carried out in spring steel.

The rod can have a round section.

These arrangements allow the stretching members to be deformed elastically in order to have a certain degree of flexibility. In each one of the relative positions of the stretching members, the bodies can as such be separated from one another with a certain clearance.

The retaining part of each one of the stretching members can comprise two retaining edges facing each other and separated from one another along the first transversal direction, with each one of the retaining edges having a concavity oriented in a direction opposite the other retaining edge.

The body of each one of the stretching members can comprise a plurality of retaining parts with each one having a separation between the retaining edges, with the separation between the retaining edges of one of the retaining parts located in the vicinity of the base being greater than the separation between the retaining edges of one of the retaining parts located at a distance from the base.

According to particular arrangements, the reduction in the efforts required to stretch the medical compression device makes it possible to automate the assistance system while still keeping it able to be carried by hand by the user.

The assistance system can further comprise a driving device housed in the support and adapted for displacing the stretching members relative to one another, and an activation member placed on the support and able to be actuated by a user in order to activate the driving device.

The support can be adapted to be carried by hand by the user.

BRIEF DESCRIPTION OF THE DRAWINGS

Other objects and advantages of the invention shall appear when reading the following description of a particular embodiment of the invention provided as a non-limiting example, with the description being given in reference to the annexed drawings wherein:

FIGS. 3 to 5 show in a plane respectively along three different orientations one of the stretching members of the assistance system of FIG. 1, FIGS. 6 and 7 show in a plane respectively along two different orientations the stretching members of the assistance system of FIG. 1 in the first (as a solid line) and second (as a mixed line) relative positions.

DETAILED DESCRIPTION

In the figures, the same references designate identical or similar elements.

Figure 1:
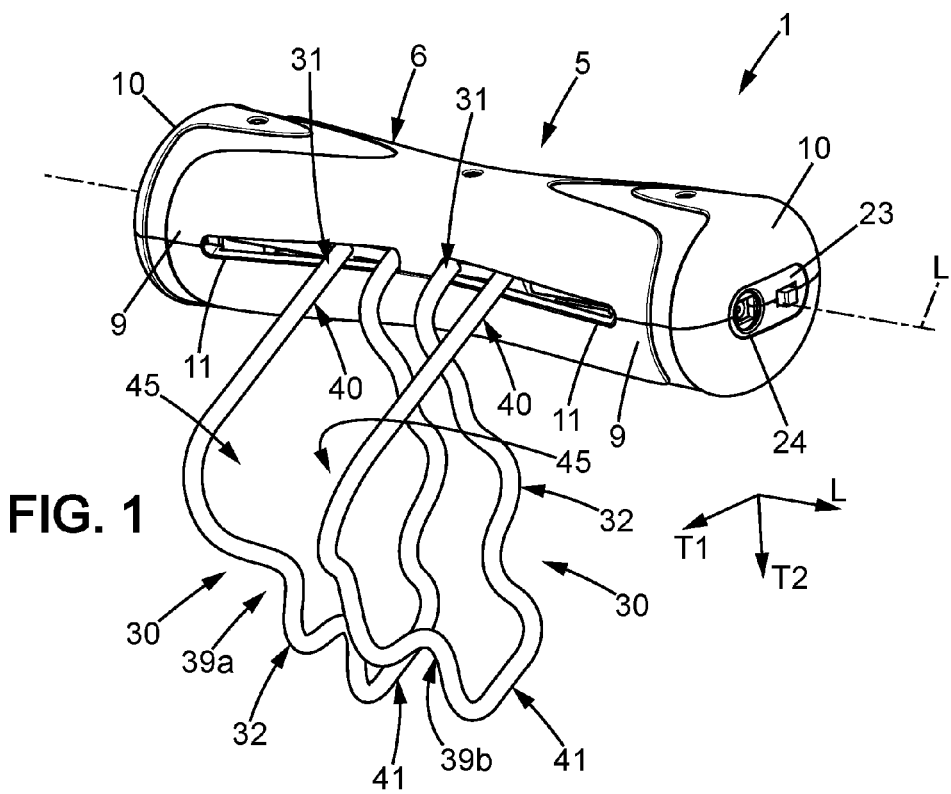
FIG. 1 shows in perspective along a first orientation an assistance system for fitting a medical compression device onto a limb of a patient according to an embodiment of the invention, with the assistance system comprising a body on which two stretching members are mounted movable in translation in relation to one another, with the stretching members being in a first relative position, brought together.
Figure 2:
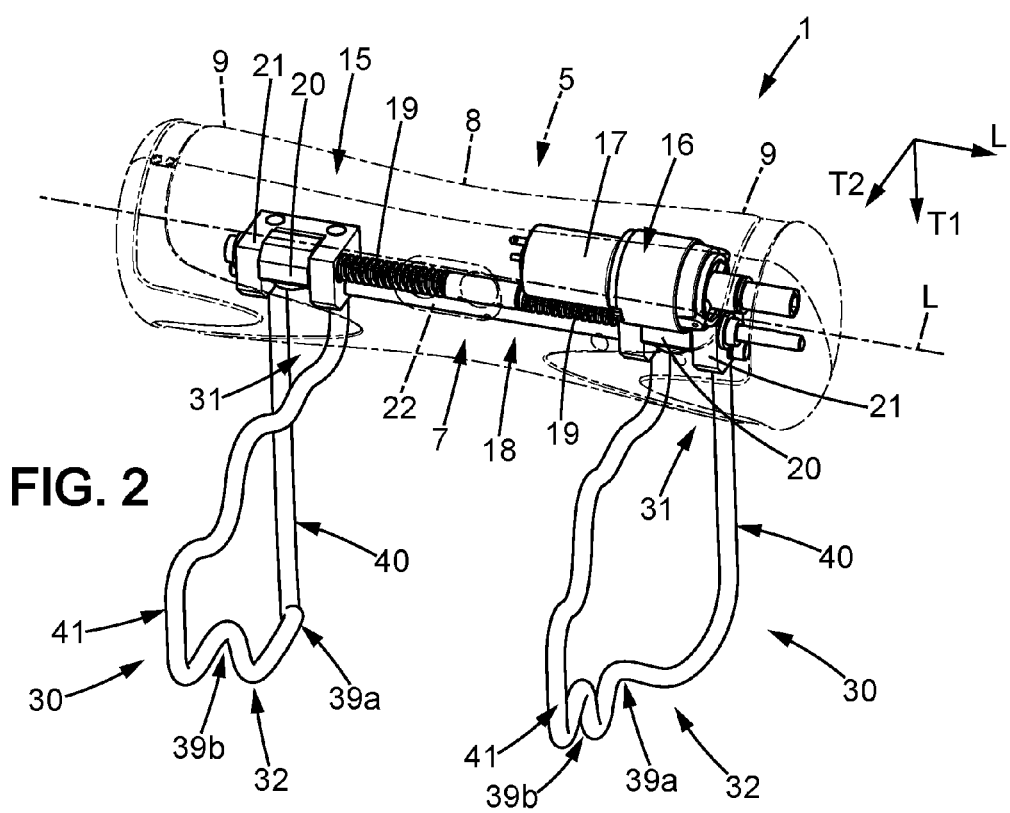
FIG. 2 shows in perspective along a second orientation of the assistance system of FIG. 1, with the stretching members being in a second relative position, spaced apart from each other, and a driving device stretching members being shown through transparency of the body.

FIGS. 1 and 2 show an assistance system 1 that makes it possible to simplify the fitting of a medical compression device onto a limb of a patient. In the embodiment shown, without being limited to it, the assistance system 1 is used to fit medical compression stockings or support stockings 4 onto a lower limb 3 of the patient.

In FIG. 1, the assistance system 1 comprises a support 5 extending along a longitudinal axis L and adapted to be worn on the hand by a user, patient or assistant. The support 5 comprises a lateral wall 6 that is tubular about the longitudinal axis L, defining an internal housing 7. In the embodiment shown, the lateral wall 6 has a central portion 8 that is thinned and that widens by moving away from the central portion 8 towards two opposite ends 9. The lateral wall 6 then generally has a hyperboloid shape that makes it possible to improve the grasping by the user. The ends 9 of the lateral wall 6 can be closed for example by means of transversal walls 10. The support 5 can then be comprised of two half-shells assembled to each other in a removable manner along a longitudinal joint plane, i.e. comprising the longitudinal axis L, in order to allow access to the internal housing 7. Alternatively, the access to the internal housing 7 of the support 5 could be obtained in any other suitable way, for example by means of at least removable cover bearing one of the transversal walls 10. The support 5 also has two slots 11 arranged on the lateral wall 6 in order to have the internal housing 7 communicate with the exterior. Each slot 11 extends along the longitudinal axis L over a portion of a length, measured along the longitudinal axis L, of half of the support 5. Alternatively, a single slot extending over a portion of the length of the support 5 could be provided.

As shown in FIG. 2 in transparency of the support 5, a driving device 15 is arranged in the internal housing 7. The driving device 15 comprises at least one actuator 16, having in the embodiment represented the form of an electric motor 17 connected to an electrical power supply more preferably portable such as a battery (not shown), and a transmission system 18, having in the embodiment shown the form of a screw-nut system. The transmission system 18 then comprises two threaded portions 19 extending parallel to the longitudinal axis L and linked to the electric motor 17 in order to be driven in rotation. The transmission system 18 also comprises two nuts 20 blocked in rotation with respect to the support 5 and mounted respectively on the threaded portions 19. Each one of the nuts 20 is mounted on a carriage 21 arranged facing one of the slots 11.

In this way, a rotation of each one of the threaded portions 19 drives a displacement in translation along the longitudinal axis L of the nut 20 and of the associated carriage 21 mounted on this threaded portion 19. In the embodiment shown, the two threaded portions are provided on the same threaded rod and respectively comprise threadings with opposite threads. Each one of the threaded portions 19 is as such driven jointly with the other threaded portion 19 in order to allow for a joint displacement of the carriages 21 in opposite directions of coming together or moving apart.

An activation member 22 in the form of two control buttons, one for each direction of displacement of the carriages 21, can then be placed on the support 5. Each one of the control buttons 22 can be actuated by the user in order to activate the driving device 15 and displace the carriages 21 along the longitudinal axis L, in one direction or the other.

Alternatively, each one of the threaded portions 19 could be driven independently from the other threaded portion 19 in order to allow for a displacement of one of the carriages 21 independently of the other carriage 21. Furthermore, the activation member 22 could have any other suitable form and comprise, for example, only one or more than two control buttons of which the actuating drives the desired displacement of the carriages 21.

As shown in FIG. 1, in order to be able to stop and turn on the driving device 15, a switch 23 that can be actuated by the user can be provided on the support 5, for example on one of the transversal walls 10. A connector 24 linked to the battery of the driving device 15 can also be provided on the support 5, for example on one of the transversal walls 10, in order to be able to recharge the battery.

The invention described with an electric driving device 15 comprising an electric motor 17, a battery and a screw-nut transmission system 18 could be implemented with any other driving device, electrical, pneumatic, hydraulic or other, comprising any suitable actuator, such as a cylinder, and, where applicable any suitable transmission system.

The assistance system 1 also comprises two stretching members 30 each comprising a connecting arm 31 extending along a first transversal direction T1, perpendicular to the longitudinal axis L, from one of the carriages 21 of the driving device 15, through one of the slots 11 of the support 5, and a body 32 extending from the connecting arm 31 along a second transversal direction T2, perpendicular to the longitudinal axis L and to the first transversal direction T1.

Figure 6:
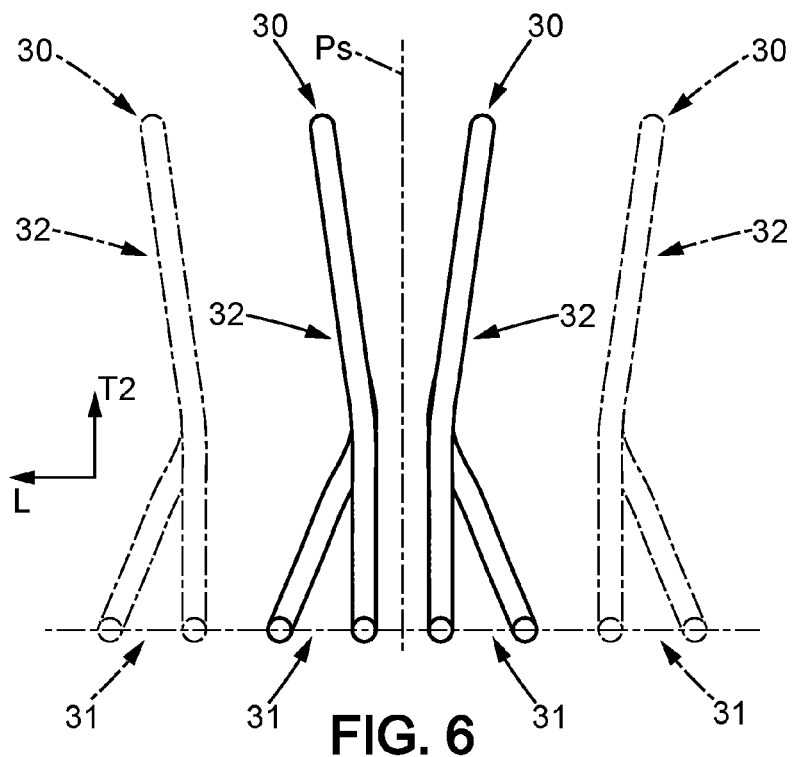
Figure 7:
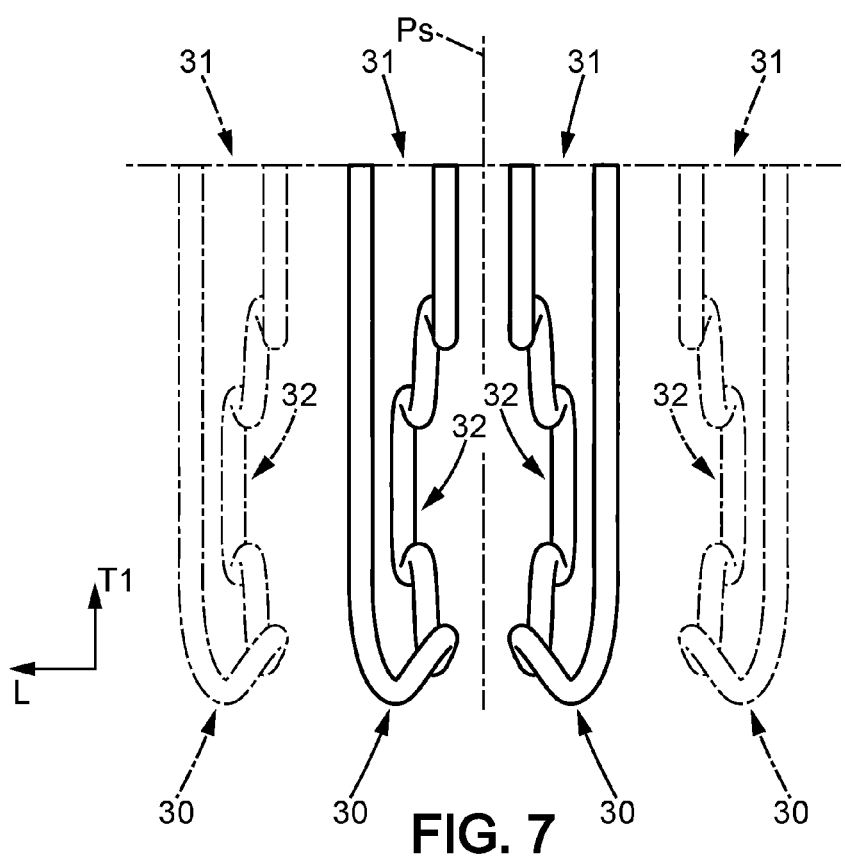

In the embodiment shown, the stretching members 30 are symmetrical in relation to one another according to a transversal plane of symmetry Ps, visible in FIGS. 6 and 7.

In FIGS. 3 to 5, each one of the stretching members 30 is formed from a single piece by the same single rod made from a material that provides it with overall rigidity once it is suitably formed as shall be described in more detail in what follows. The material can nevertheless be chosen to authorise an elastic deformation of the body 32 relative to the connecting arm 31 in such a way that each one of the stretching members 30 can have a certain degree of flexibility along the longitudinal axis L. The rod can, moreover, have an external surface that is adapted to facilitate a setting into place of the support stockings 4 on the stretching member 30 and/or provide a maintaining of the support stockings 4 on the stretching member 30 as shall appear in the rest of the description. For example, the rod can have a round section, be made of metal, such as spring steel, covered with a coating, in particular made of plastic material. The rod can then be formed by folding or arching. Alternatively, the rod can be formed by moulding, where applicable followed by any suitable treatment.

The connecting arm 31 of the stretching member 30 is comprised of two branches of the rod, one external 33 and the other internal 34, extending in the same horizontal plane, along the first transversal direction T1 by being spaced apart from one another along the longitudinal axis L.

The body 32 of the stretching member 30 is comprised of a bow 35 of the rod extending globally perpendicularly to the horizontal plane of the external 33 and internal 34 branches, along the second transversal direction T2, between the external 33 and internal 34 branches of the rod. Alternatively, the connecting arm 31 of the stretching member 30 could be comprised of a single branch to which the bow 35 would be suitable linked.

The body 32 comprises:
- a base branch 36 extending along the first transversal direction T1, in the extension of the external branch 33 for forming a base 40 of the body 32 of the stretching member 30,
- two vertical branches 37 extending respectively from the base branch 36 and the internal branch 34, globally along the second transversal direction T2, converging towards one another until they are joined opposite the base branch 36 for forming a distal end 41 of the stretching member 30.

The vertical branches 37 of the body 32 comprise two first retaining edges 38a, arranged in the vicinity of the base branch 36, facing each other and spaced apart from one another along the first transversal direction T1. Each one of the first retaining edges 38a has a concavity oriented in a direction opposite the other first retaining edge 38a, outwards, in such a way that the first retaining edges 38a are brought closer to one another, while maintaining a first separation between them. The first retaining edges 38a as such form a first retaining part 39a arranged between the base 40 and the distal end 41 of the stretching member 30 and adapted to receive and retain a portion of the support stockings 4, at least on a fitting opening of the latter, on the stretching member 30.

The vertical branches 37 of the body 32 also comprise two second retaining edges 38b, arranged at a distance from the base branch 36, facing each other and spaced apart from one another along the first transversal direction T1. Each one of the second retaining edges 38b has a concavity oriented in a direction opposite the other second retaining edge 38b, outwards, in such a way that the second retaining edges 38b are brought closer to one another, while still maintaining a second separation between them, less than the first separation. The second retaining edges 38b as such form a second retaining part 39b arranged between the base 40 and the distal end 41 of the stretching member 30 and adapted to receive and to retain a portion of the support stockings 4, at least on the fitting opening of the latter, on the stretching member 30.

Alternatively, the body 32 of each stretching member 30 could comprise a single retaining part or more than two retaining parts of which the separation between the retaining edges decreases when moving away from the base 40.

In FIGS. 4 and 5, the first 39a and second 39b retaining parts are arranged respectively in first Pt1 and second Pt2 transversal planes, i.e. perpendicular to the longitudinal axis L, separated inwards, i.e. towards the internal branch 34, relative to a third transversal plane Pt3 wherein extends the base 40 of the body 32. The first Pt1 and second Pt2 transversal planes are, moreover, spaced apart inwards relative to a fourth transversal plane Pt4 wherein extends the distal end 41 of the body 32.

In particular, the vertical branch 37 of the body 32 adjoining the base branch 36 comprises a first portion between the base branch 36 and the first retaining edge 38a, said first portion is inclined from the third transversal plane Pt3 comprising the base 40 of the body 32 to a fifth transversal plane Pt5 comprising the internal branch 34 of the connecting arm 31. The vertical branch 37 of the body 32 adjoining the internal branch 34 comprises a first portion between the internal branch 34 and the first retaining edge 38a, said first portion extends in the fifth transversal plane Pt5. The first retaining part 39a is then arranged substantially in the fifth transversal plane Pt5 confounded with the first transversal plane Pt1. The vertical branches 37 of the body 32 are then elbowed outwards, i.e. towards the external branch 33, in such a way as to respectively have second portions located in the same inclined plane Pi about an axis parallel to the first transversal direction T1. The second transversal plane Pt2 comprising the second retaining part 39b is then located between the third transversal plane Pt3 comprising the base 40 and the first transversal plane Pt1 comprising the first retaining part 38a and the internal branch 34. The fourth transversal plane Pt4 comprising the distal end 41 of the body 32 is located between the third transversal plane Pt3 comprising the base 40 and the second transversal plane Pt2 comprising the second retaining part 39b.

The stretching member 30 as such has a concavity turned outwards and carried out, in the embodiment shown, by a fold extending along the first transversal direction T1 on the first retaining part 39a.

The body 32 of the stretching member 30, delimited by the bow 35 of the rod, is hollow and has a recess 45 along the second transversal direction T2 that extends, in the embodiment shown, from the base 40 to the distal end 41.

In FIGS. 6 and 7, the stretching members 30 are mounted on carriages 21, facing one another, with the internal branches 34 of the connecting arm 31 being placed facing one another.

The internal branch 34 of the connecting arm 31 of each stretching member 30 is then spaced apart from the external branch 33 along the longitudinal axis L. Furthermore, each one of the retaining parts 39a, 39b of the first of the stretching members 30 is offset along the longitudinal axis L towards the corresponding retaining part 39a, 39b of the second stretching member 30 relative to the base 40 of the first stretching member 30. In the same way, each one of the retaining parts 39a, 39b of the first stretching member 30 is offset along the longitudinal axis L towards the corresponding retaining part 39a, 39b of the second stretching member 30 in relation to the distal end 41 of the first stretching member 30. The first stretching member 30 has, moreover, a concavity oriented outwards, i.e. in a direction opposite the second stretching member 30, on the first retaining part 38a. The separation along the longitudinal axis L between the bases 40 of the stretching members 30 is therefore greater than the separation along the longitudinal axis L between the retaining parts 39a, 39b. Similarly, the separation along the longitudinal axis L between the distal ends 41 of the stretching members 30 is greater than the separation along the longitudinal axis L between the retaining parts 39a, 39b.

The invention has been described in relation with an embodiment wherein each one of the stretching members 30 has the particular conformation according to the invention in such a way as to be able to form in turn the first stretching member 30 and the second stretching member 30. The invention is not, however, limited to such an embodiment and also applies to an embodiment wherein only one of the stretching members 30 has a particular conformation according to the invention and forms the first stretching member 30, with the other stretching member forming the second stretching member 30. Furthermore, the stretching member or members 30 could be carried out in any other suitable way. In particular, only the body 32 could be formed by the rod of which ends are linked to internal and external connecting elements extending parallel in relation to one another along the first transversal direction T1 in such a way that the separation between the external connecting elements is greater than that of the internal connecting elements.

By actuating the control button or buttons 22, the carriages 21 can be displaced in translation along the longitudinal axis L in relation to one another in order to place the stretching members 30 in a suitable relative position chosen from a plurality of relative positions. In particular, the stretching members 30 can be placed in a first relative position, brought together and centred in relation to support 5, appearing in sold lines in the FIGS. 6 and 7 and corresponding to the position shown in FIG. 1. Alternatively, in the brought together position, the stretching members 30 can come into contact with one another on internal branches 34 or with the first retaining part 39a. They could also be off-centred in relation to support 5. The stretching members 30 can be spaced apart from one another to a second relative position, appearing as a mixed line in FIGS. 6 and 7 and corresponding to the position shown in FIG. 2.

Figure 8:
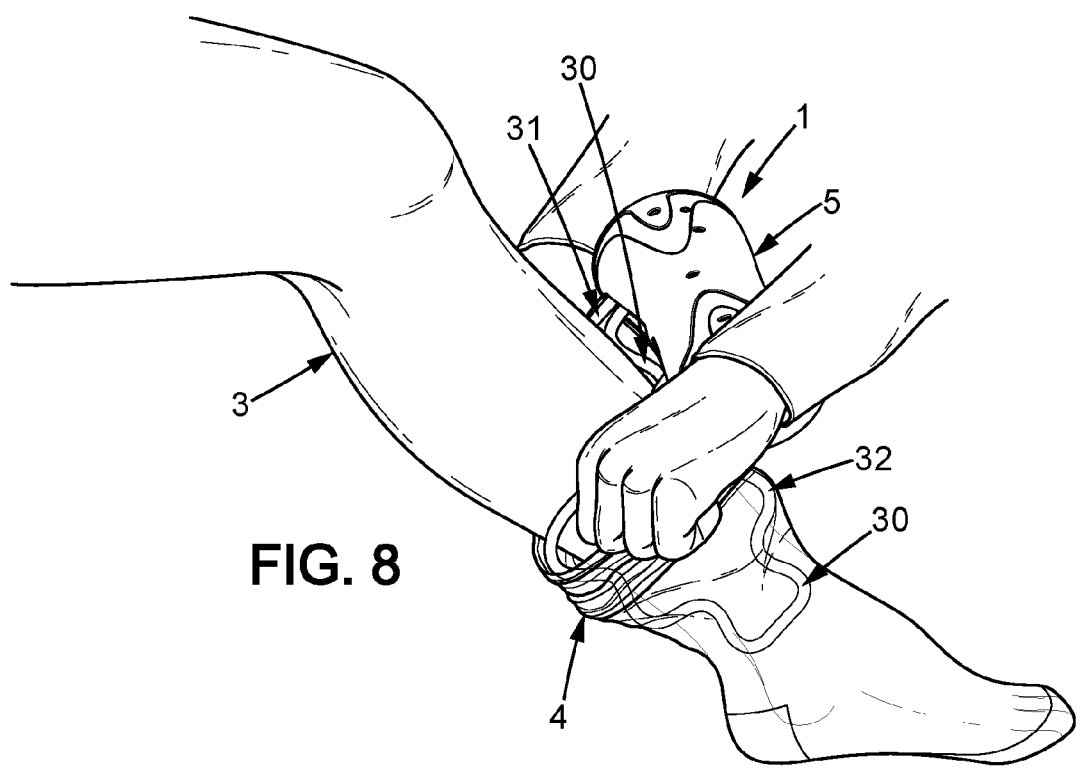
FIG. 8 shows in perspective the fitting of a medical compression device onto a limb of a patient using the assistance system of FIG. 1.

As shown in FIG. 8, after having placed them in the first relative position, brought together, the stretching members 30 are introduced into the fitting opening of the support stockings 4 via the distal end 41 until at least one portion of the support stockings 4 in the vicinity of the fitting opening is positioned on the first retaining parts 39a of the bodies 32 of the stretching members 30. The stretching members 30 can then be separated from one another by actuating the control buttons 22 in order to stretch the support stockings 4 until the relative position is reached that makes it possible to pass the foot between the bases 40 of the bodies 32 of the stretching members 30. The introduction of the foot into the space between the stretching members 30, in the recesses 45, completes the separation of the support stockings 4, by a gentle surrounding of its tarsal and metatarsal portion. The separation between the distal ends 41 of the bodies 32 of the stretching members 30 also simplifies the passage of the foot between the stretching members 30. Due to a certain degree of flexibility of the stretching members 30, the bodies 32, slightly brought close together under the effect of a force exerted by the support stockings 4, can be elastically recalled to a state of rest and move slightly away from each other as the support stockings 4 are fitted onto the lower limb 3 of the patient and the force that it exerts decreases.

The invention claimed is:

1. Assistance system for fitting a medical compression device onto a limb of a patient, the medical compression device having a fitting opening, with the assistance system comprising:
   a support extending along a longitudinal axis,
   two stretching members each comprising a connecting arm extending from the support along a first transversal direction, and a body extending from the connecting arm along a second transversal direction, with the body of each one of the stretching members comprising a base linked to the connecting arm and at least one retaining part separated from the base and whereon at least one portion of the medical compression device in the vicinity of the fitting opening is intended to be positioned, with the stretching members being mounted on the support facing one another and moveable with respect to one another in translation along the longitudinal axis,
   wherein the retaining part and the base of at least a first of the stretching members extend respectively in transversal planes perpendicular to the longitudinal axis, with the transversal plane containing the retaining part of the first stretching member being offset along the longitudinal axis towards the retaining part of the other, second, stretching member relative to the transversal plane containing the base of said first stretching member, the body of the first stretching member having a recess along the second transversal direction at least on the retaining part, and wherein the first stretching member comprises:

a shaped rod for forming the body and comprising the base of the body, an external connecting element extending along the first transversal direction for forming a part of the connecting arm, the base of the body being linked to the external connecting element, and an internal connecting element extending along the first transversal direction parallel to the external connecting element, the internal connecting element being separated from the external connecting element along the longitudinal axis the direction of the second stretching member, the internal connecting element forming another part of the connecting arm to which the rod is linked opposite the base.

2. Assistance system according to claim 1, wherein the body of the first stretching member has a concavity oriented in a direction opposite the second stretching member on the retaining part of said first stretching member.

3. Assistance system according to claim 2, wherein the retaining part of the first stretching member has a fold extending along the first transversal direction.

4. Assistance system according to claim 1, wherein the body of each one of the stretching members has a distal end opposite the base, the retaining part of the first stretching member being offset along the longitudinal axis towards the retaining part of the second stretching member relative to the distal end of said first stretching member.

5. Assistance system according to claim 4, wherein the distal end of the first stretching member is arranged between two transversal planes wherein extend respectively the base and the retaining part of said first stretching member.

6. Assistance system according to claim 1, wherein the first stretching member is formed from a single piece by the shaped rod, the rod comprising an external branch forming the external connecting element, and a bow extending globally along the second transversal direction for forming the body, the bow comprising a base branch extending in the extension of the external branch for forming the base of the body.

7. Assistance system according to claim 6, wherein the rod further comprises an internal branch forming the internal connecting element.

8. Assistance system according to claim 6, wherein the rod is made from spring steel.

9. Assistance system according to claim 6, wherein the rod has a round section.

10. Assistance system according to claim 1, wherein the retaining part of each one of the stretching members comprises two retaining edges facing and separated from one another along the first transversal direction, with each one of the retaining edges having a concavity oriented in a direction opposite the other retaining edge.

11. Assistance system according to claim 1, wherein the body of each one of the stretching members comprises a plurality of retaining parts each one having a separation between the retaining edges, with the separation between the retaining edges of one of the retaining parts located in the vicinity of the base being greater than the separation between the retaining edges of one of the retaining parts located at a distance from the base.

12. Assistance system according to any of claim 1, further comprising a driving device housed in the support and adapted to displace the stretching members relative to one another, and an activation member placed on the support and that can be actuated by a user in order to activate the driving device.

13. Assistance system according to claim 12, wherein the support is adapted to be carried by hand by the user.

* * * * *